United States Patent
Elshout

(10) Patent No.: US 8,419,507 B2
(45) Date of Patent: *Apr. 16, 2013

(54) TEXTURIZING SURFACES

(75) Inventor: Robert Elshout, Katwijk (NL)

(73) Assignee: Mentor Worldwide LLC, Santa Barbara, CA (US)

( * ) Notice: Subject to any disclaimer, the term of this patent is extended or adjusted under 35 U.S.C. 154(b) by 91 days.

This patent is subject to a terminal disclaimer.

(21) Appl. No.: 12/957,333

(22) Filed: Nov. 30, 2010

(65) Prior Publication Data

US 2011/0070356 A1    Mar. 24, 2011

Related U.S. Application Data

(63) Continuation of application No. 11/533,528, filed on Sep. 20, 2006, now Pat. No. 7,867,061.

(51) Int. Cl.
*B24C 1/00* (2006.01)

(52) U.S. Cl.
USPC ........................... 451/40; 623/7; 623/8

(58) Field of Classification Search ............ 451/40; 623/7, 8

See application file for complete search history.

(56) References Cited

U.S. PATENT DOCUMENTS

| | | | | |
|---|---|---|---|---|
| 3,702,519 A * | 11/1972 | Rice et al. | ............. | 451/29 |
| 5,344,494 A * | 9/1994 | Davidson et al. | ............ | 134/7 |
| 5,344,654 A * | 9/1994 | Rueger et al. | ............ | 424/423 |
| 5,354,338 A * | 10/1994 | Ledergerber | ............ | 623/8 |
| 5,525,275 A * | 6/1996 | Iversen et al. | ............ | 264/28 |
| 5,607,607 A * | 3/1997 | Naiman et al. | ............ | 219/121.68 |
| 5,645,740 A * | 7/1997 | Naiman et al. | ............ | 219/121.68 |
| 5,826,586 A * | 10/1998 | Mishra et al. | ............ | 128/898 |
| 5,965,076 A * | 10/1999 | Banks et al. | ............ | 264/219 |
| 6,005,164 A * | 12/1999 | Johansson et al. | ............ | 623/23.55 |
| 7,105,116 B2 * | 9/2006 | Bellin et al. | ............ | 264/131 |
| 7,867,061 B2 * | 1/2011 | Elshout | ............ | 451/40 |
| 2005/0216094 A1 * | 9/2005 | Prewett | ............ | 623/23.74 |
| 2010/0042223 A9 * | 2/2010 | Zinger et al. | ............ | 623/18.11 |

* cited by examiner

*Primary Examiner* — Maurina Rachuba

(57) ABSTRACT

Methods for applying surface texture to the exterior of bodily implants, as well as implants made by the methods described.

10 Claims, 1 Drawing Sheet

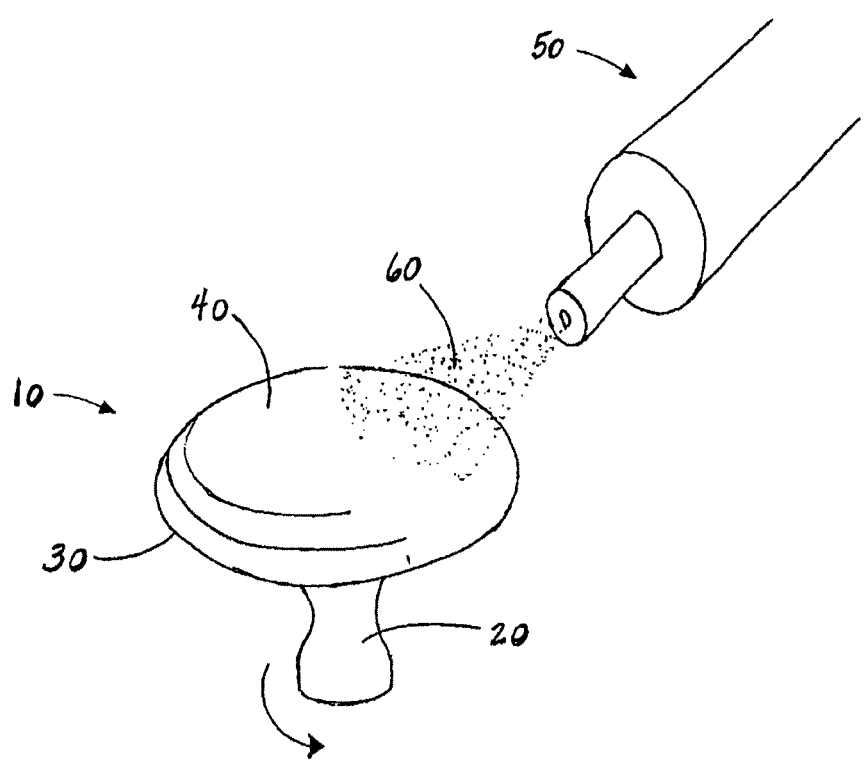

TEXTURIZING SURFACES

CROSS REFERENCE TO RELATED APPLICATIONS

This application is a continuation of U.S. application Ser. No. 11/533,528, filed Sep. 20, 2006, the entire disclosure of which is expressly incorporated herein by reference.

TECHNICAL FIELD

This document relates to methods and materials involved in applying a surface texture to devices such as bodily implants (e.g., breast implants).

BACKGROUND

A capsule of scar tissue can form around an implant after it is placed in the body. This is a natural reaction of the body to protect itself from the introduction of a foreign object. The formation of this scar capsule is referred to as capsular contracture. Capsular contracture that may result after breast augmentation surgery can result in hardening of the breasts, which may be painful and can require additional surgery.

SUMMARY

Textured implants can reduce the chance of capsular contracture. The textured surface of these implants can promote tissue adherence to the implant, decreasing the amount of scar tissue that grows. In addition, tissue adherence to an implant can help maintain proper implant positioning and prevent movement of the implant within the breast.

Current methods for applying texture to an implant, however, can be labor intensive and expensive. For example, current methods can include forming an implant shell on a mandrel, removing the shell from the mandrel, placing the shell on a second mandrel or other form, and then applying the surface texture. The hole left in the shell by the first mandrel may be expanded during placement on the second mandrel or other form, resulting in shells having holes of different sizes and shapes that cannot be patched in an automated manner.

This document provides methods and materials related to texturizing the outer surface of implant devices, as well as devices texturized by the methods provided herein. The methods provided herein include contacting the outer surface of a device with solid carbon dioxide ($CO_2$), otherwise known as dry ice. The physical collision of dry ice pellets with the outer surface of an implant, as well as the temperature difference between the dry ice and the implant, can create dimples in the outer surface of the implant and cause the dry ice to evaporate. These methods can be advantageous in that they can permit texture to be applied to the entire surface of an implant, and can be used to make implants from a single material, thus obviating the stress that can result between layers when different types of materials are used. These methods also can be economical from both monetary and material standpoints, and can be automated. In addition, these methods can result in a patch hole of standardized size, thus allowing for automation of the patching process.

In one aspect, this document features a method for texturizing a bodily implant having an outer surface. The method can include contacting the outer surface of the bodily implant with dry ice particles. The bodily implant can be a breast implant. The dry ice particles can have a maximum diameter of about 1 mm to about 1.5 mm. The dry ice particles can be passed through a screen prior to contacting the outer surface of the bodily implant. The screen can define openings having a maximum width of about 1 mm to about 2 mm. The bodily implant can have an inner cured layer of an elastomer and an outer uncured layer of the elastomer in a solvent, wherein the method comprises contacting the outer uncured layer with the dry ice particles. The outer uncured layer can comprise from about 10 percent to about 30 percent solids. The outer uncured layer can have a devolatilization time of about 8 minutes to about 10 minutes. The dry ice particles can be directed at the outer surface of the bodily implant by a stream of air at a pressure of about 5 bar.

In another aspect, this document features a bodily implant having an outer surface with a surface texture applied by contacting the outer surface with dry ice particles. The bodily implant can be a breast implant. The dry ice particles can have a maximum diameter of about 1 mm to about 1.5 mm. The dry ice particles can have been passed through a screen prior to contacting the outer surface of the bodily implant. The screen can define openings having a maximum width of about 1 mm to about 2 mm. The surface area can have been applied by coating the bodily implant with an outer uncured layer of an elastomer in a solvent (e.g., an outer uncured layer comprising from about 10 percent to about 30 percent solids, having a devolatilization time of about 8 minutes to about 10 minutes, or both), and contacting the outer uncured layer with the dry ice particles. The dry ice particles can have been directed at the outer surface of the bodily implant by a stream of air at a pressure of about 5 bar.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawing, and from the claims.

DESCRIPTION OF DRAWINGS

FIG. 1 is a depiction of the outer shell of a breast implant on a mandrel as it is contacted by dry ice particles ejected from a nozzle.

DETAILED DESCRIPTION

Elastomeric articles such as shells for bodily implants (e.g., breast implants) can be made using a mandrel having a mold in the desired form connected to a shaft. The mold can be repeatedly dipped in or coated with an elastomeric compound (e.g., polyurethane, Bioflex™, silicone, or latex) dispersed in a solvent (e.g., xylene, heptane, tetrahudrofurane/dioxin, N,N-dimethylformamide, N,N-dimethylacetamide, naptha, or water). Between coatings, the mandrel can be heated to allow the solvent to evaporate. The mandrel also can be heated at the end of the procedure to allow the elastomeric compound to set or cure.

The methods provided herein can be used to texturize the exterior surface of such bodily implants. These methods include contacting the exterior surface of an implant with dry ice pellets, which can create imprints on the surface of the device and then evaporate. For example, the shell of a breast implant can be formed on a mandrel by covering the mandrel with an elastomer (e.g., silicone). The shell may be cured, or the shell may not be cured. In some cases, the shell can be cured, and then a further layer of polymer can be applied and not cured. While still on the mandrel (e.g., during evaporation of solvent), the shell can be contacted (e.g., blasted) with pellets of dry ice. Dry ice is inert, and is available in medical grade. The pellets can be directed at one or more particular areas of the shell, or can be directed at the entire surface of the shell. Because the shell can be texturized while still on the mandrel, rather than being removed from the mandrel and then placed on another device for texturizing, the hole in the shell from the mandrel stem can have the same or similar dimensions as holes in other implant shells generated using the same method. In other words, shell manufacture can be standardized to allow for automated patching of the shells.

Any suitable device can be used to contact an implant with dry ice (e.g., dry ice pellets). For example, a commercially available system such as a CryoClean system from Hoek Loos (Schiedam, Holland) can be used. Such a system can, for example, use compressed air to propel particles of dry ice at high velocity, thus achieving an impact energy sufficient to create imprints on surfaces. Dry ice pellets can be pre-produced, or can be produced on demand from liquid $CO_2$. When dry ice pellets impact, they can compress and mushroom out into a high velocity "snow," and then can instantly sublimate back into their natural state as a gas, leaving no residue. This can create a compression tension wave. The $CO_2$ gas can expand to nearly 800 times the volume of the pellet in milliseconds, resulting in a small series of micro-explosions at the impact point.

A system such as a CryoClean system can be equipped with any suitable mechanism for achieving dry ice pellets of a size appropriate to give a desired surface texture to an implant. For example, dry ice pellets can be passed from a holding tank through a hose, and out a nozzle aimed at an implant. In some embodiments, the nozzle can contain a means for reducing the size of the pellets. For example, a screen (e.g., a wire mesh screen) can be positioned within a nozzle, such that dry ice pellets exiting the device must pass through the screen. In some cases, more than one (e.g., two, three, four, or five) screens can be positioned within the nozzle of a device, such that the dry ice pellets must pass through all of the screens before exiting the nozzle.

Depending on the size of the screen(s), the pellets can be broken into smaller particles of a particular maximum size. By controlling the size of the dry ice pellets, homogeneous texturing of the implant can be achieved. For example, a screen with larger openings can be used to produce particles of dry ice with a larger maximum size, increasing the size of the imprints made in the implant surface. A screen can have openings of any shape (e.g., square, circular, oval, rectangular, triangular, or any other shape), and can contain wire of any suitable thickness. For example, a screen can include wire having a thickness of about 0.08 mm, 0.1 mm, 0.2 mm, 0.3 mm, 0.4 mm, 0.5 mm, 0.6 mm, 0.7 mm, 0.8 mm, 0.9 mm, 1 mm, or more than 1 mm. The openings in a screen can have a maximum width or diameter of, for example, about 0.2 mm to about 5 mm (e.g., about 0.3 mm, about 0.5 mm, about 0.7 mm, about 1 mm, about 1.2 mm, about 1.5 mm, about 1.7 mm, about 2 mm, about 2.3 mm, about 2.5 mm, about 2.8 mm, about 3 mm, about 3.2 mm, about 3.5 mm, about 3.7 mm, about 4 mm, about 4.5 mm, or about 5 mm). A screen having openings with a maximum width or diameter of about 1 mm to about 3 mm, for example, can result in dry ice particles having a maximum width of about 1 mm to about 3 mm. As used herein, the term "maximum width" or "maximum diameter" with respect to an opening in a screen refers to the longest straight line distance that can be measured between two points on the perimeter of the opening. As used herein, the term "maximum width" or "maximum diameter" with respect to a dry ice pellet refers to the longest straight line distance that can be measured through the pellet between two points on the exterior surface of the pellet.

Other parameters also can affect the surface texture created as a result of dry ice contacting a surface. For example, the percent solids (viscosity) of the substance applied as the outer layer of an implant shell can be adjusted. The percent solids can be, for example, from about 0% to about 50%, about 2.5% to about 40%, about 5% to about 35%, about 10% to about 35%, or about 15% to about 25%. A higher viscosity, particularly at a consistent devolatilization time, can result in a coarser texture, for example, upon dry ice blasting. Devolatilization time also can be adjusted to control the surface texture. During evaporation of the solvent, the viscosity of the outer layer of the implant can rise. Thus, devolatilization time can be an important parameter for controlling the structure of the surface texture. The devolatilization time can be, for example, from about 1 minute to about 20 minutes (e.g., about 2 minutes to about 6 minutes, about 5 minutes to about 13 minutes, about 6 minutes to about 8 minutes, about 7 minutes to about 12 minutes, about 8 minutes to about 10 minutes, about 10 minutes to about 15 minutes, or about 15 minutes to about 20 minutes). In addition, the air pressure of the application system (e.g., the CryoClean system) can be adjusted. For example, a higher air pressure can result in greater velocity of the dry ice particles at impact with the implant surface, which can affect the resulting structure of the surface texture. The air pressure can be, for example, from about 2 bar to about 10 bar (e.g., about 2 bar, about 3 bar, about 4 bar, about 5 bar, about 6 bar, about 7 bar, about 8 bar, about 9 bar, or about 10 bar). Any or all of the parameters described herein can be adjusted to, for example, control the depth and or pattern of the surface texture.

The methods provided herein can include moving the mandrel holding the implant or moving the device used to direct the dry ice particles at the implant. For example, a mandrel can be inverted, moved back and forth, or rotated during a texturizing procedure, or the nozzle of the device used to direct the dry ice particles can be moved around the mandrel, or up and down or back and forth with respect to the mandrel as it directs dry ice particles toward the implant. In some cases, both the mandrel and the nozzle can be moved during a texturizing procedure. Such movement can, for example, facilitate production of a homogenous surface texture over the entire outer surface of an implant shell. The movement can be simultaneous with surface texture generation. In some cases, surface texture can be generated on one portion of an implant, the dry ice flow can be stopped, the mandrel and/or the nozzle can be moved, and the flow of dry ice particles can be resumed such that surface texture is generated on another portion of the implant.

FIG. 1 is a depiction of one embodiment of a texturizing procedure as provided herein. Mandrel 10 can include stem 20 and mold 30, with mold 30 covered by implant shell 40. Nozzle 50 can direct dry ice particles 60 toward the surface of implant shell 40. As shown in FIG. 1, mandrel 10 can be rotated (e.g., in the direction of the arrow) as implant shell 40 is contacted by dry ice particles 60.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for texturizing a bodily implant, comprising contacting an outer uncured surface of an elastomer of said bodily implant with dry ice particles being directed by a stream of air, and creating imprints on the outer uncured surface.

2. The method of claim 1, wherein said dry ice particles have a maximum diameter of about 1 mm to about 1.5 mm.

3. The method of claim 1, wherein said dry ice particles are passed through a screen prior to contacting said outer surface of said bodily implant.

4. The method of claim 1, wherein said bodily implant includes an inner cured layer of an elastomer.

5. The method of claim 1, wherein said dry ice particles are directed at said outer uncured surface of said bodily implant by a stream of air at a pressure of about 5 bar.

6. A method for texturizing a bodily implant having an outer surface, comprising contacting an untextured surface of the outer surface of said bodily implant with dry ice particles being directed by a stream of air, and creating imprints on the untextured surface of said outer surface of said bodily implant.

7. The method of claim 6, wherein said dry ice particles have a maximum diameter of about 1 mm to about 1.5 mm.

8. The method of claim 6, wherein said dry ice particles are passed through a screen prior to contacting said outer surface of said bodily implant.

9. The method of claim 6, wherein said bodily implant comprises an inner cured layer of an elastomer and an outer uncured layer of an elastomer in a solvent, wherein the method comprises contacting said outer uncured layer with said dry ice particles.

10. The method of claim 6, wherein said dry ice particles are directed at said outer uncured surface of said bodily implant by a stream of air at a pressure of about 2 bar to about 10 bar.

* * * * *